(12) United States Patent
Heede (10) Patent No.: US 11,457,992 B2
(45) Date of Patent: Oct. 4, 2022

(54) STORAGE ASSEMBLY FOR A MEDICAL DEVICE

(71) Applicant: Stryker European Operations Holdings LLC, Kalamazoo, MN (US)

(72) Inventor: Andreas Heede, Neumünster (DE)

(73) Assignee: Stryker European Operations Holdings LLC, Kalamazoo, MI (US)

( * ) Notice: Subject to any disclaimer, the term of this patent is extended or adjusted under 35 U.S.C. 154(b) by 112 days.

(21) Appl. No.: 16/316,270

(22) PCT Filed: Jul. 8, 2016

(86) PCT No.: PCT/US2016/041518
§ 371 (c)(1),
(2) Date: Jan. 8, 2019

(87) PCT Pub. No.: WO2018/009215
PCT Pub. Date: Jan. 11, 2018

(65) Prior Publication Data
US 2019/0231468 A1    Aug. 1, 2019

(51) Int. Cl.
*A61B 50/30* (2016.01)
*A61B 50/33* (2016.01)
*A61B 50/00* (2016.01)
*A61B 50/20* (2016.01)
*B23P 19/00* (2006.01)
*B21D 22/02* (2006.01)

(52) U.S. Cl.
CPC .............. *A61B 50/30* (2016.02); *A61B 50/00* (2016.02); *A61B 50/20* (2016.02); *A61B 50/33* (2016.02); *B21D 22/02* (2013.01); *B23P 19/00* (2013.01); *A61B 2050/3008* (2016.02); *Y10T 29/49995* (2015.01)

(58) Field of Classification Search
CPC ............................... A61B 50/30; A61B 50/33
See application file for complete search history.

(56) References Cited

U.S. PATENT DOCUMENTS 3,822,783 A * 7/1974 Mortensen ......... B65D 73/0014
206/480
4,153,160 A * 5/1979 Leigh ..................... A61B 50/33
206/370

(Continued)

OTHER PUBLICATIONS

International Search Report and Written Opinion dated Sep. 16, 2016, for PCT/US2016/041518, 3 pages.

Primary Examiner — Christopher M Koehler
(74) Attorney, Agent, or Firm — Lerner, David, Littenberg, Krumholz & Mentlik, LLP (57) ABSTRACT

The invention relates to a storage assembly for at least a medical device, an insert and tray assembly comprising such storage assembly, and a manufacturing method for such storage assembly. The storage assembly comprises a sheet material. The sheet material comprises at least a recess in a planar portion of the sheet metal and at least a holding structure. The recess is configured to surround the medical device to be stored. The holding structure protrudes into the direction of the recess and is bent out of the sheet material planar portion to extend below the sheet material planar portion, so that the holding structure is configured to hold the medical device to be received from above relative to the sheet material planar portion.

18 Claims, 5 Drawing Sheets

(56) References Cited

U.S. PATENT DOCUMENTS

| | | | | |
|---|---|---|---|---|
| 4,512,466 A * | 4/1985 | Delang | A61B 50/20 | 206/370 |
| 5,098,391 A * | 3/1992 | Pantages | A61B 50/33 | 206/563 |
| 5,339,955 A * | 8/1994 | Horan | A61B 50/33 | 206/350 |
| 5,353,929 A * | 10/1994 | Foster | A61B 50/33 | 206/364 |
| 5,384,103 A * | 1/1995 | Miller | A61C 19/02 | 16/438 |
| 5,485,917 A * | 1/1996 | Early | B65D 5/725 | 206/363 |
| 5,681,539 A * | 10/1997 | Riley | A61L 2/26 | 206/370 |
| 5,690,226 A | 11/1997 | N'Guyen | | |
| 5,779,053 A * | 7/1998 | Parti | A61B 50/33 | 206/370 |
| 5,848,693 A * | 12/1998 | Davis | A61B 50/33 | 206/370 |
| 5,984,097 A * | 11/1999 | Kalinski | A61B 17/06114 | 206/366 |
| 6,193,932 B1 * | 2/2001 | Wu | A61L 2/07 | 206/210 |
| 6,382,575 B1 * | 5/2002 | Frush | A61L 2/26 | 211/85.13 |
| 6,405,863 B1 * | 6/2002 | Dhindsa | B65D 1/36 | 206/370 |
| 6,436,357 B1 * | 8/2002 | Frieze | A61L 2/26 | 206/263 |
| 6,783,004 B1 * | 8/2004 | Rinner | A61B 17/8875 | 206/368 |
| 6,957,909 B1 * | 10/2005 | Dingeldein | B65D 75/36 | 220/221 |
| 7,441,655 B1 * | 10/2008 | Hoftman | A61B 50/20 | 206/370 |
| 8,567,603 B2 * | 10/2013 | Liccardo | A61F 2/0095 | 206/438 |
| 2011/0278188 A1 * | 11/2011 | Steinhardt | A61F 2/18 | 206/438 |
| 2013/0206626 A1 * | 8/2013 | Schindel | A61F 2/30942 | 206/438 |
| 2014/0078854 A1 * | 3/2014 | Head | B01F 11/0005 | 366/111 |
| 2014/0346071 A1 * | 11/2014 | Genosar | B65D 25/02 | 206/438 |
| 2015/0122682 A1 * | 5/2015 | Kerboul | A61B 50/20 | 206/370 |
| 2016/0287901 A1 * | 10/2016 | Dumaine | A61B 17/3468 | |
| 2017/0224434 A1 * | 8/2017 | Schwartzbauer | A61B 50/33 | |
| 2018/0028703 A1 * | 2/2018 | McLaughlin | B65D 1/38 | |
| 2018/0116747 A1 * | 5/2018 | Matityahu | A61B 17/744 | |
| 2018/0214233 A1 * | 8/2018 | Termanini | A61F 2/0095 | |
| 2018/0221171 A1 * | 8/2018 | Termanini | A61B 50/33 | |
| 2018/0271632 A1 * | 9/2018 | Berg | A61B 50/30 | |
| 2019/0110851 A1 * | 4/2019 | Barnes | A61B 50/33 | |
| 2019/0201569 A1 * | 7/2019 | Rhodes | A61L 2/26 | |
| 2019/0262577 A1 * | 8/2019 | Anderson | A61B 1/00144 | |
| 2019/0365495 A1 * | 12/2019 | Heath | A61B 50/33 | |
| 2020/0360549 A1 * | 11/2020 | Neveu | A61L 2/24 | |
| 2021/0007822 A1 * | 1/2021 | Pruckner | A61B 50/34 | |

* cited by examiner

STORAGE ASSEMBLY FOR A MEDICAL DEVICE

CROSS-REFERENCE TO RELATED APPLICATIONS

The present application is a national phase entry under 35 U.S.C. § 371 of International Application No. PCT/US2016/041518 filed Jul. 8, 2016, which is incorporated herein by reference.

BACKGROUND OF THE INVENTION

The invention relates to a storage assembly for a medical device, an insert and tray assembly comprising such storage assembly, and a manufacturing method for such storage assembly.

U.S. Pat. No. 4,512,466 A discloses a surgical instrument organizer for receiving a plurality of stacked instruments of the hinged type. It comprises a base, a pair of finger ring posts extending upwardly from the base for extension through respective finger rings of the instruments, a shaft separator extending upwardly from the base and between the shafts of the instruments and a tip separator also extending upwardly from the base and between jaws of the instrument. The organizer supports the instruments during sterilization thereof, and a forward end and sides of the base extend outwardly of the instrument tips to protect the same against contact and damage. After sterilization, the instruments may be carried on the organizer to an operating theater and removed therefrom as required.

BRIEF SUMMARY OF THE INVENTION

There may be a need to provide an improved storage assembly for a medical device, which is in particular more efficient.

The problem of the present invention is solved by the subject-matters of the independent claims; wherein further embodiments are incorporated in the dependent claims. It should be noted that the aspects of the invention described in the following apply also to the storage assembly for at least a medical device, the insert and tray assembly comprising such storage assembly, and the manufacturing method for such storage assembly.

According to the present invention, a storage assembly for a medical device is presented. The storage assembly comprises a sheet material. The sheet material comprises a recess formed in a planar portion of the sheet metal and at least one holding structure. The recess is configured to surround the medical device to be stored. The holding structure protrudes into the recess and is bent out of the planar portion of the sheet metal to extend below the planar portion of the sheet metal, so that the holding structure is configured to support the medical device when inserted into the recess from above the sheet material planar portion.

In other words, a storage solution for one or more medical devices e.g. instruments or implants is provided. Therefore, e.g. a piece of metal such as a planar sheet material is provided with a recess, cavity or hole. The recess surrounds the medical device to be stored and may in particular surround the longitudinally aligned medical device.

The sheet material further comprises a holding structure for holding or fixing the medical device in the recess. The holding structure may one or more bent or folded flap(s), ribs, straps or tap(s). Therefore, the holding structure protrudes on the one hand into the recess, and is on the other hand bent out of the sheet material planar portion or a plane of the sheet material in a downward direction relative to the sheet material planar portion or plane. The holding structure then extends below the sheet material planar portion or plane. The sheet material plane is the plane formed by the planar portion of the sheet material.

The medical device may be inserted into the recess in the same downward direction as the holding structure is bent. The medical device is inserted from above the sheet material planar portion or plane, while the holding structure extends below the sheet material planar portion or plane. The medical device may be contacted and held by the holding structure. The terms "above" and "below" are defined to be on different sides of the sheet material and its sheet material plane.

The storage assembly according to the invention is a very efficient solution for storing of one or more medical devices. The storage assembly is very light, safe and can be easily and cost effectively manufactured. The storage assembly allows for the storage of the medical device(s) with a much reduced contact area between the storage assembly and the medical device(s), which allows a nearly complete treatment of the medical device(s) by means of e.g. a sterilization and/or cleaning liquid.

The recess may reproduce or correspond to the outer contour of the medical device to be stored. The recess may in particular reproduce or correspond to the outer contour of the longitudinally aligned medical device.

The recess may be larger than the medical device, so that the medical device can be fully inserted into the recess. The recess may be in particular larger than a maximum cross section of the medical device taken along a longitudinal axis. The recess may, however, be smaller than a maximum cross section of the medical device taken along a longitudinal axis. The medical device needs then to be held by the holding structure in a manner that a larger portion of the medical device remains outside the recess.

In an example, the medical device is one of a group comprising a medical instrument and a medical implant. In an example, the holding structure is configured to hold the medical device in an open condition to allow a most global access and treatment of all surfaces of the medical device.

In an example, the sheet material comprises a plurality of holding structures to improve a storage of the medical device(s). In an example, the sheet material comprises a plurality of recesses and a plurality of holding structures to store a plurality of medical devices. In an example, the plurality of recesses provides an unambiguous assignment between each medical device and each recess. As a consequence, each medical device only matches to or fits into the one and only correct recess. Thereby, also a missing of a medical device can be easily determined.

In an example, the storage assembly is configured to be sterilized. The sterilization may be done by heat, radiation and/or chemicals. The storage assembly may therefore be resistant to e.g. 60 to 100° C., γ-radiation and/or acids. The storage assembly may be made of metal.

In an example, the holding structure is at least a pin contacting a point of the medical device. In another example, the holding structure is a continuous profile surrounding a portion of the medical device. The holding structure may have essentially a U-shape or a V-shape. A non-perpendicular and in particular a slanted angle may be formed between the bent holding structure and the sheet material plane. In an example, the angle between the bent holding structure and the sheet material plane is between 1 and 89°, preferably between 30 and 60°, and more preferably between 40 and 50°.

The shape of the recess may comprise a grip portion to ease a pulling of the medical device out of the storage assembly. In an example, the plurality of recesses and holding structures are configured to hold the plurality of medical devices at the same level. This may mean that the plurality of medical devices abuts with the same distance to the sheet material plane in either an upward or a downward direction. In an example, the holding structure is biased to form an elastic holding structure. The holding structure may also be provided with a snap-in feature to fix the medical device.

In an example, the sheet material further comprises a support structure configured to support the storage assembly. The support structure may act as feet of the storage assembly and provide a distance to a surface on which the storage assembly is placed. The support structure may be implemented by the holding structure. Then, the longest downward bent parts of the holding structure may contact the surface supporting the storage assembly and act at the same time as feet of the storage assembly and as holding structure for holding the medical device. The support structure may form an angle of about 90° relative to the sheet material planar portion.

However, the support structure may also be implemented by additional parts, flaps or taps separate to the holding structure. These additional or separate parts of the support structure may be arranged at corners and/or a boundary of the storage assembly. The support structure may be part of the sheet material and may be bent downward out of the sheet material plane to extend below the sheet material plane to form feet of the storage assembly. As the medical device is inserted from above the sheet material plane, the support structure then extends on a side of the sheet material plane different to the insertion side of the medical device into the recess.

The support structure may also be bent upward out of the sheet material plane to extend above the sheet material plane to form arms of the storage assembly to be hung or clamped into e.g. a tray. The support structure then extends on the insertion side of the sheet material plane, where the medical device is inserted into the recess. In both cases, the support structure may be bent out of the sheet material plane for about 90° relative to the sheet material plane.

In an example, the storage assembly further comprises a protective structure arranged at the holding structure and/or at the sheet material in the recess thereof. The protective structure may be configured to protect and hold a rod-shaped portion of the medical device. The rod-shaped portion may be the medical device itself or a part of it. The protective structure may be one or more flexible and/or elastic e.g. rubber parts attached to the holding structure and/or the sheet material in the recess to contact or surround at least portions of the medical device. The protective structure may protect in particular a rod-shaped medical device or at least a rod-shaped portion of the medical device from being unintentionally released from the storage assembly and/or from being scratched or damaged by the sheet material. The protective structure may be in particular suitable for a small, delicate and/or longitudinal medical device.

According to the present invention, also an insert and tray assembly is presented. The insert and tray assembly comprises the storage assembly as described above and a tray, wherein the storage assembly is configured to be inserted into the tray.

In an example, the tray comprises only a frame configured to surround the storage assembly. In an example, the tray comprises a bottom. The bottom may be provided additionally or instead of the frame. The bottom may be provided as a kind of basket or grid with holes or windows to ease a flow of liquid through the storage assembly.

In an example, the tray comprises a cover to close and cover the insert and tray assembly so that the medical device(s) cannot be lost, untidy or contaminated. Both, the storage assembly and the tray may be made of metal.

According to the present invention, also a manufacturing method for a storage assembly for at least a medical device is presented. The manufacturing method comprises the following steps:

a) providing a sheet material,
b) forming, such as by laser cutting, at least one recess in a planar portion of the sheet material and at least a holding structure in the sheet material, wherein the recess is configured to surround the medical device to be stored and wherein the holding structure protrudes into the recess, and
c) bending the holding structure out of the planar portion of the sheet material to extend below the planar portion of the sheet material, so that the holding structure is configured to support the medical device when inserted from above the sheet material planar portion.

In an example, the manufacturing method further comprises forming a support structure in the sheet material, and a bending the support structure out of the sheet material plane so that the support structure is configured to support the medical device. In an example, the support structure is formed by laser cutting.

In an example, the storage assembly and the tray are manufactured together from the same sheet material. Above listened steps may then be performed to manufacture the storage assembly and surrounding sheet material may be used to manufacture a frame forming the tray.

It shall be understood that the storage assembly for at least a medical device, the insert and tray assembly comprising such storage assembly, and the manufacturing method for such storage assembly according to the independent claims have similar and/or identical preferred embodiments, in particular, as defined in the dependent claims. It shall be understood further that a preferred embodiment of the invention can also be any combination of the dependent claims with the respective independent claim.

BRIEF DESCRIPTION OF THE DRAWINGS

Exemplary embodiments of the invention will be described in the following with reference to the accompanying drawings.

DETAILED DESCRIPTION

Figure 1:
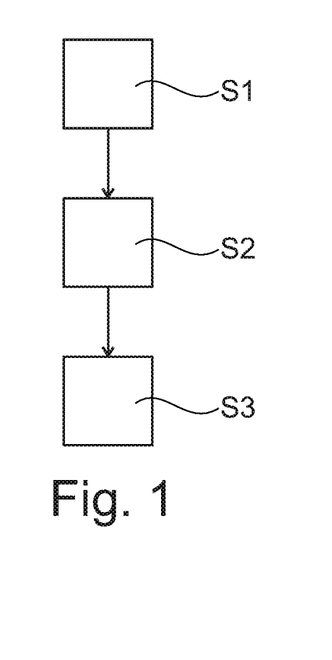
FIG. 1 shows a schematic overview of the steps of a manufacturing method for a storage assembly for at least a medical device.
Figure 2:
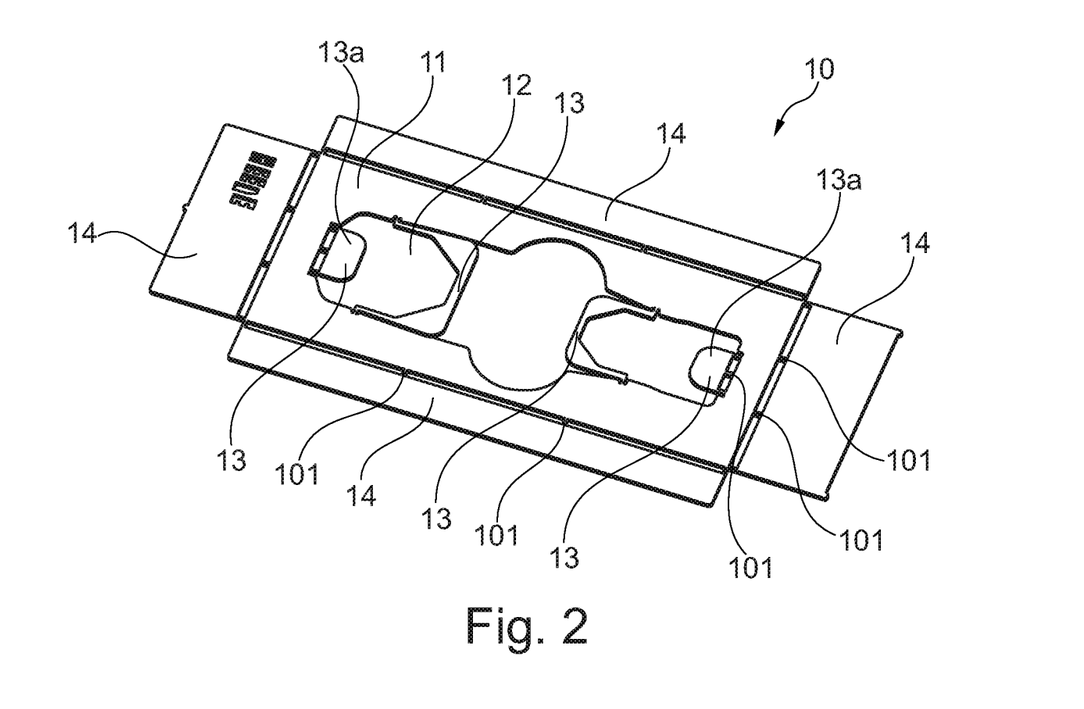
FIGS. 2 to 4 show intermediate results of the manufacturing steps and a storage assembly according to the invention.

FIG. 1 shows a schematic overview of the steps of a manufacturing method for a storage assembly or storage tray 10 for at least a medical device 20. Referring to FIGS. 1 and 2, the method comprises the following steps In a first step S1, providing a preferably planar sheet material 11.

In a second step S2, forming at least one recess 12 and at least one holding structure 13 in the sheet material 11, wherein the recess 12 is larger than the outer contour of the medical device 20 (not shown in FIG. 1) to be stored and wherein the holding structure 13 protrudes into the recess 12. The recess 12 and holding structure 13 may be formed by laser cutting.

In a third step S3, the holding structure 13 is bent about portions 101 out of a planar portion S or plane S of the sheet metal 11 to extend below the sheet material planar portion S or plane S, so that the holding structure 13 is configured to hold the medical device 20 to be received from above the sheet material planar portion S or plane S.

Optionally, step S2 further comprises forming a support structure 14 in the sheet material 11 and a bending of the support structure 14 out of the sheet material planar portion S or plane S so that the support structure 14 is configured to support the medical device 20. The forming is preferably also by laser cutting.

Small connecting portions or tabs 101 are left during the laser cutting process to facilitate bending of the holding structure 13 and the support structure 14 relative to the sheet material 11. The portions 101 are wide enough to permit the downward deflection of the holding structure 13 and the support structure 14 without fracture. The connecting portions 101 maintain the holding structure 13 and the support structure 14 integral with the top surface of sheet material 11. Stop structures 13a are also formed by the laser cutting. After downward bending, the stop structures 13a serve to keep the instrument or implant in position along the length of the formed storage assembly 10. Again the laser cutting leaves connecting points 101 between the stop structures 13a to maintain connection to the remainder of the sheet material 11 while allowing easy downward bending.

The bending of the holding structure 13, the stop structures 13a and the support structure 14 can be performed by an appropriately formed die (not shown) which forces the initially planar support structure 14, holding structure 13 and stop structures 13a downward into a shape matching the instrument or implant to be inserted and forces the holding structure 13, the stop structures 13a and the support structure 14 downwardly to between preferably 30° and 90° with respect to the sheet material plane S.

Figure 3:
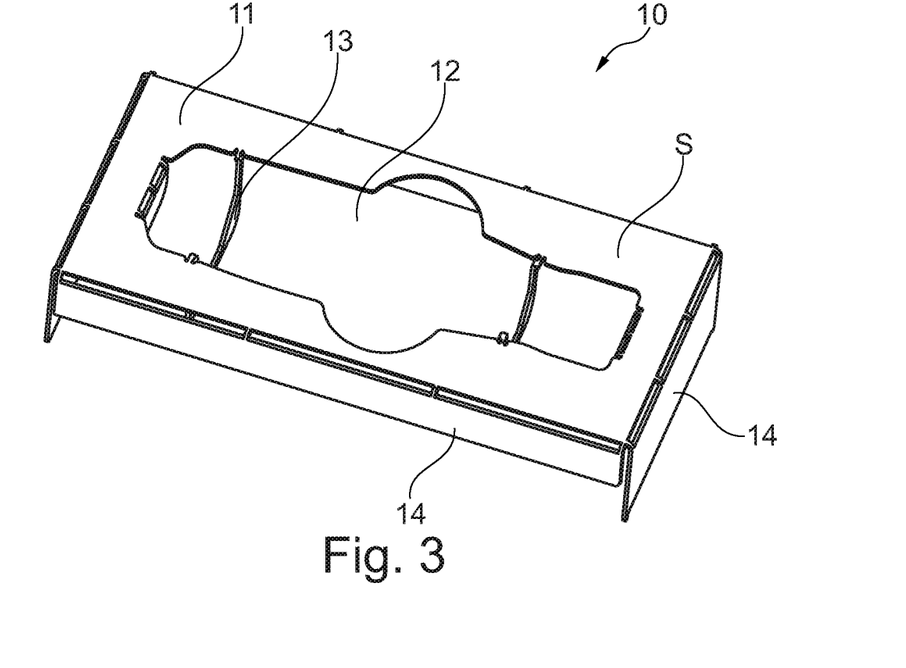
Figure 4:
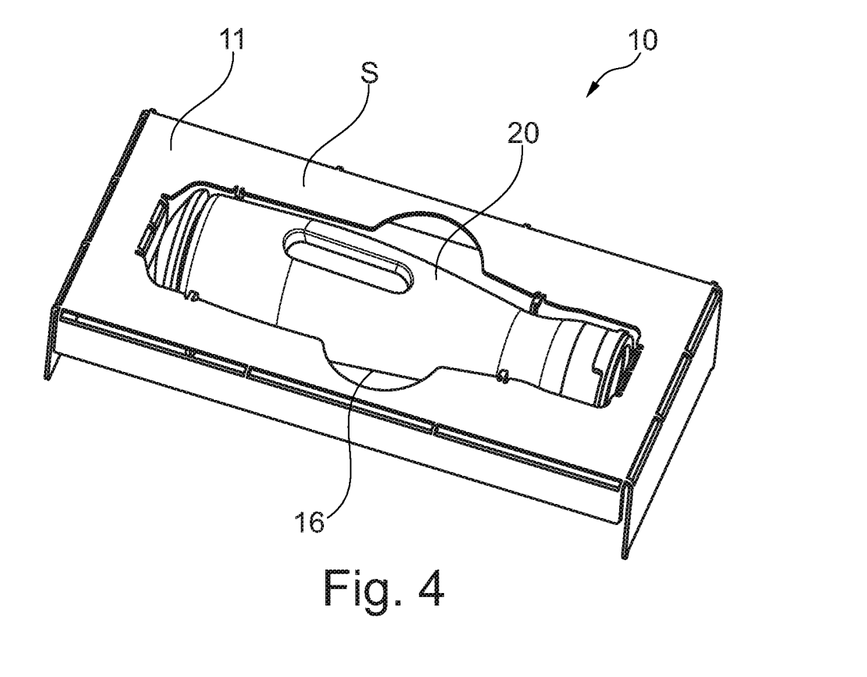

FIGS. 2 to 4 show intermediate results of the manufacturing steps up to a use of a finalized storage assembly 10 for a medical device 20.

In FIG. 2, the sheet material 11 is provided with the recess 12, holding structures 13 and support structures 14. The holding structures 13 are in the sheet material plane S and protrude into the recess 12. Also the support structures 14 are in the sheet material plane S and are arranged around the boundaries of the storage assembly 10. The sheet material plane is the plane formed by the sheet material.

In FIG. 3, the holding structures 13 and stop structures 13a are bent in a downwards direction out of the sheet material plane S to extend below the sheet material plane S and to hold the medical device 20 to be received also in the downwards direction but from above the sheet material plane S. Also the support structures 14 are bent downwards out of the sheet material plane S to act as feet of the storage assembly 10 and provide a distance to a ground on which the storage assembly 10 is placed. FIG. 3 thereby shows schematically and exemplarily an embodiment of the storage assembly 10 according to the invention. The storage assembly 10 comprises the sheet material 11, which comprises the recess 12, several holding structures 13, two stop structures 13a, and four support structures 14. The holding structures 13 are here continuous profiles or supports surrounding portions of the medical device 20 and act to cradle the medial device 20 to protect it from damage during sterilization and shipping.

In FIG. 4, the medical device 20 is downwardly inserted from above the sheet material plane S in to the recess 12 and the holding structures 13. The shape of the recess 12 corresponds to, but is larger than the outer contour of the medical device 20 in its longitudinal extension. The recess 12 comprises two grip portions 16. Large portions of the medical device 20 are now contacted and held by the holding structure 13 below the sheet material plane S.

As a result, a storage solution for the medical device 20 is provided, which is very efficient, safe, light and can be easily manufactured. The storage assembly 10 allows the storage of the medical device 20 with a much reduced contact area between the storage assembly 10 and the medical device 20, which allows a nearly complete treatment of the medical device 20 by means of e.g. a sterilization and/or cleaning liquid.

In preferred embodiments, the sheet material 11 is stainless steel. Other metals can be used if sufficiently strong and ductile or bendable. The metal needs to be able to be sufficiently ductile or bendable to form the preferably arcuate holding structures 13 and the preferably planar support structures 14. The thickness of the sheet material 11 may be between 4 and 0.5 mm, preferably between 3 and 0.5 mm, and more preferably about 2 mm.

FIGS. 5 to 8 show intermediate results of the manufacturing steps up to a use of the finalized storage assembly 10 for several medical devices 20. The medical devices 20 are here medical instruments.

Figure 5:
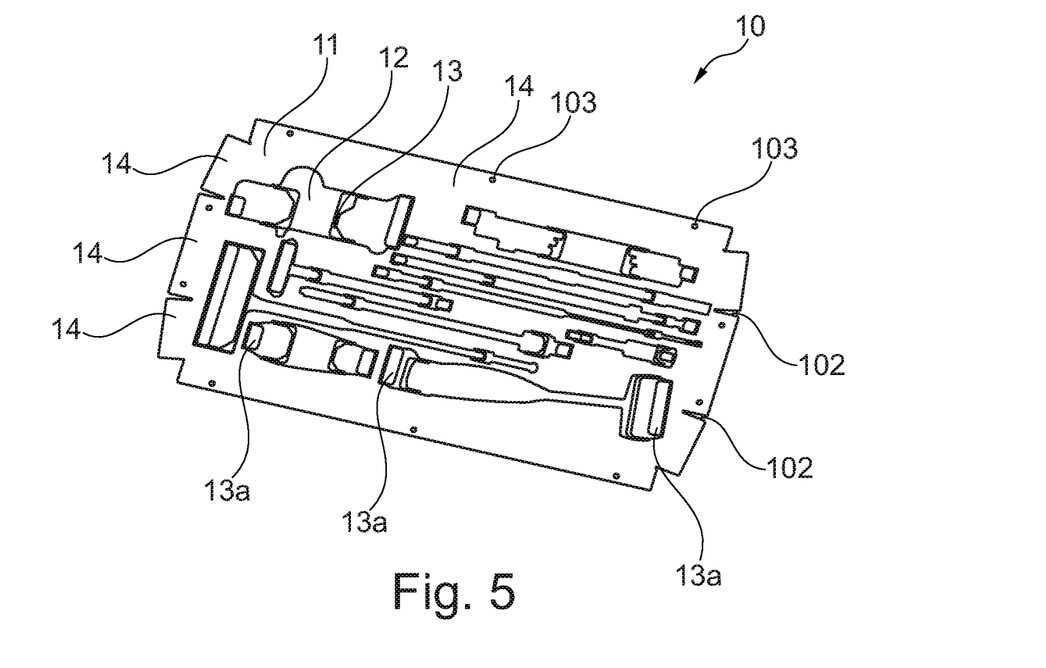
FIGS. 5 to 8 show intermediate results of the manufacturing steps and an insert and tray assembly according to the invention.

In FIG. 5, the sheet material 11 is provided with several recesses 12, each having preferably two holding structures 13, two end stops 13a, and support structures 14 extending around the periphery of the sheet metal plate. The holding structures 13 lie in the sheet material plane S and protrude into the recesses 12. Also the support structures 14 are in the sheet material plane S and are arranged around the boundaries of the storage assembly 10. Slits 102 are provided to ease downward bending. Holes 103 are provided for suitable hangers or clips (not shown).

Figure 6:
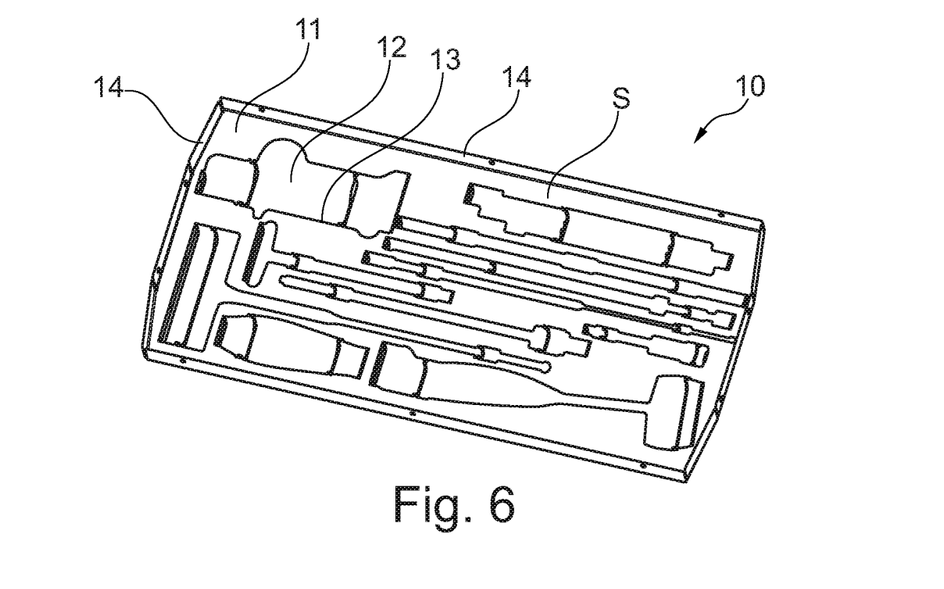

In FIG. 6, there is shown an alternate embodiment where the storage assembly 10 may be hung in a storage case or tray 2. Case or tray 2 has perforations to allow the sterilizing media to contact the instruments. As discussed above, the holding structures 13 are bent in a downwards direction out of the sheet material plane S to extend below the sheet material plane S and to hold the medical device 20 in the downwards direction. The holding structures 13 are here again have continuous profiles or surrounding portions of the medical device 20. The support structures of this embodiment structure, such as flaps, ribs or straps are here bent in an upward direction out of the sheet material plane S to form arms of the storage assembly 10 to be hung or clamped into the tray 2. FIG. 6 thereby shows schematically and exemplarily an embodiment of a storage assembly 10 according to the invention.

Figure 7:
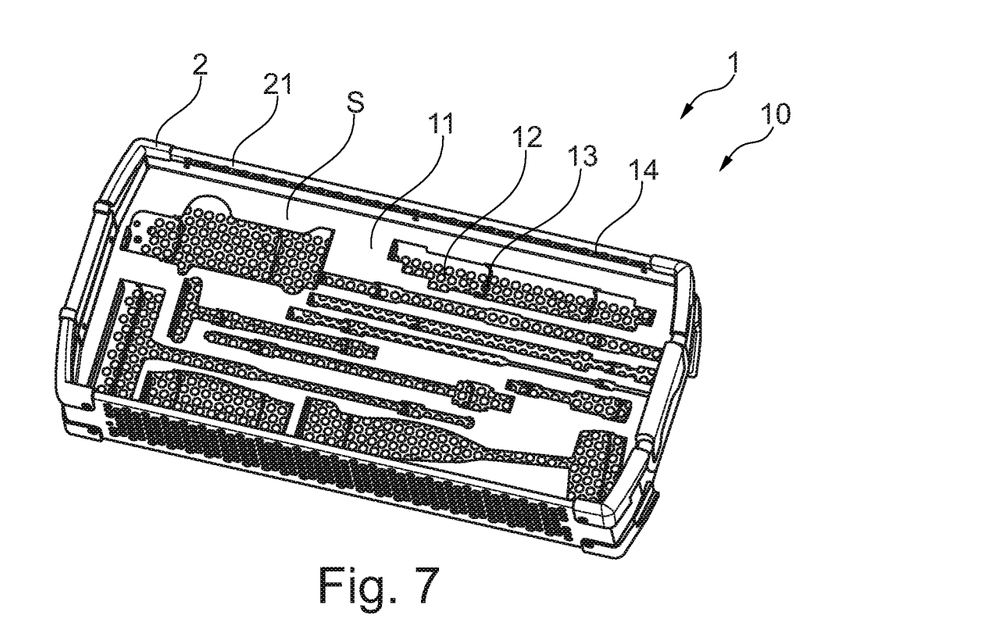

In FIG. 7, the storage assembly 10 is inserted into the case or tray 2. The perforations of tray 2 can be seen through the recesses 12 of the planar sheet metal 11. The tray 2 comprises a frame 21 surrounding the storage assembly 10. FIG. 7 thereby shows schematically and exemplarily an embodiment of an insert and tray assembly 1 according to the invention. The insert and tray assembly 1 comprises the storage assembly 10 and the tray 2.

Figure 8:
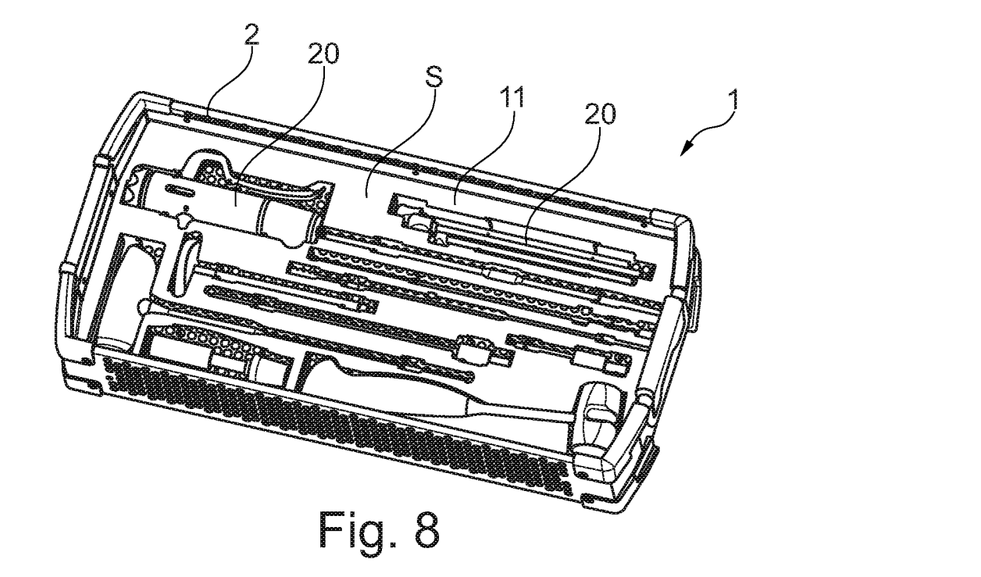

In FIG. 8, several medical devices 20 are inserted in to the recesses 12 and holding structures 13 in downwards direction from above the sheet material plane S. Portions of the medical devices 20 are now contacted and held by the holding structures 13 below the sheet material plane S. The recesses 12 correspond to, but are larger than the outer contours of the longitudinally arranged medical devices 20. Thereby, the plurality of recesses 12 provide an unambiguous assignment between each medical device 20 and each recess 12. The storage assembly 10 and the tray 2 are made of metal and can be sterilized by heat, radiation and/or chemicals.

Figure 9:
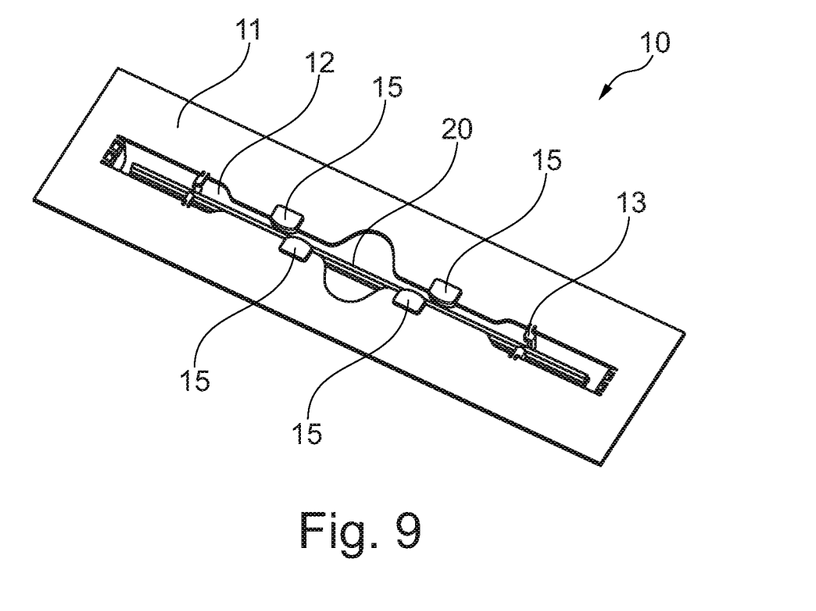
FIG. 9 shows a further embodiment of a storage assembly according to the invention.

FIG. 9 shows another embodiment of the storage assembly 10 with a sheet material 11 comprising one recess 12 and several holding structures 13. There are no support structures. The holding structures 13 are bent in a downwards to hold the medical device 20. Here, the storage assembly 10 further comprises protective structures 15 arranged at the sheet material 11 in the recess 12 of the sheet material 11. The protective structures 15 protect and hold a rod-shaped medical device 20. The protective structures 15 are flexible rubber parts contacting portions of the medical device 20.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A manufacturing method for a storage assembly for at least a medical device, comprising the following steps:
   providing a sheet material;
   inserting at least a recess in a planar portion of the sheet material and at least a holding structure in the sheet material, the at least one holding structure extending in a plane of the planar portion of the sheet material;
   wherein the recess is configured to surround entirely the medical device to be stored and wherein the holding structure protrudes into the recess, and
   bending the holding structure out of the planar portion of the sheet material to extend below the planar portion of the sheet material, so that the holding structure is configured to support the medical device when inserted into the recess from above relative to the sheet material planar portion.

2. The manufacturing method according to claim 1, further comprising inserting of a support structure in the sheet material and bending of the support structure out of the sheet material planar portion, so that the support structure is configured to support the medical device.

3. The manufacturing method according to claim 2, wherein the support structure forms an angle of about 90° relative to the planar portion of the sheet material.

4. The manufacturing method according to claim 1, wherein the inserting is a laser cutting.

5. The manufacturing method of claim 1, further comprising at least first and second connecting portions extending between the planar portion and the at least one holding structure, wherein the at least one holding structure is bent about the at least first and second connecting portions such that the at least one holding structure is transverse to the at least a recess.

6. The manufacturing method according to claim 1, wherein the shape of the recess corresponds to an outer contour of the medical device to be stored.

7. The manufacturing method according to claim 1, wherein the holding structure forms an angle between 30° and 60° relative to the planar portion of the sheet material.

8. The manufacturing method according to claim 1, wherein the holding structure is a pin contacting a point of the medical device or a continuous profile surrounding a portion of the medical device.

9. The manufacturing method according to claim 1, further comprising arranging a protective structure at the sheet material, wherein the protective structure is configured to protect and hold a rod-shaped portion of the medical device.

10. The manufacturing method according to claim 1, wherein the storage assembly is made of metal.

11. The manufacturing method according to claim 1, wherein the storage assembly is configured to be sterilized.

12. The manufacturing method according to claim 1, wherein the medical device is one of a group consisting of a medical instrument and a medical implant.

13. The manufacturing method according to claim 1, wherein the holding structure is configured to hold the medical device in an open condition.

14. The manufacturing method according to claim 1, wherein the sheet material comprises a plurality of recesses and holding structures to store a plurality of medical devices.

15. The manufacturing method according to claim 14, wherein the plurality of recesses and holding structures are configured to hold the plurality of medical devices at the same level.

16. A manufacturing method for a storage assembly for at least a medical device, comprising the following steps:
   providing a sheet material;
   inserting at least a recess in a planar portion of the sheet material and at least a holding structure in the sheet material, the at least one holding structure extending in a plane of the planar portion of the sheet material;
   wherein the recess is configured to surround the medical device to be stored and wherein the holding structure protrudes into the recess, wherein the recess is larger than the medical device such that the medical device is configured to be fully inserted into the recess, and
   bending the holding structure out of the planar portion of the sheet material to extend below the planar portion of the sheet material, so that the holding structure is configured to support the medical device when inserted into the recess from above relative to the sheet material planar portion.

17. The manufacturing method of claim 16, wherein the recess is larger than a maximum cross section of the medical device taken along a longitudinal axis.

18. The manufacturing method of claim 5, wherein the first connecting portion extends from a first edge of the at least a recess and the second connecting portion extends from a second edge of the at least a recess.

* * * * *